United States Patent
Kastenbaum

(12) 
(10) Patent No.: US 6,685,472 B2
(45) Date of Patent: Feb. 3, 2004

(54) TOOL FOR REMOVING SOFT TISSUE GROWTH AROUND A DENTAL IMPLANT

(76) Inventor: Fred Kastenbaum, 1 Gracie Sq., New York, NY (US) 10028

( * ) Notice: Subject to any disclaimer, the term of this patent is extended or adjusted under 35 U.S.C. 154(b) by 94 days.

(21) Appl. No.: 10/000,631

(22) Filed: Nov. 1, 2001

(65) Prior Publication Data

US 2003/0082497 A1 May 1, 2003

(51) Int. Cl.[7] .............................. A61C 3/00; A61C 3/02
(52) U.S. Cl. ......................................... 433/75; 433/144
(58) Field of Search .......................... 433/72, 75, 141, 433/144

(56) References Cited

U.S. PATENT DOCUMENTS 2,569,844 A * 10/1951 Berliner ...................... 433/144
3,108,376 A * 10/1963 Weinger ...................... 433/144

* cited by examiner

Primary Examiner—Cary E. O'Connor
(74) Attorney, Agent, or Firm—Darby & Darby

(57) ABSTRACT

A dental instrument having a blade and an elongated guide connected to the blade. The guide is sized to fit within the bore of a dental implant and is placed at a predetermined radial location with respect to the blade. The guide may selectively translate in a direction parallel to the cutting plane of the blade. The instrument includes a geometric step or a conical surface integrated into the guide so as to prevent the guide from being inserted further than a predetermined distance into the implant.

12 Claims, 2 Drawing Sheets

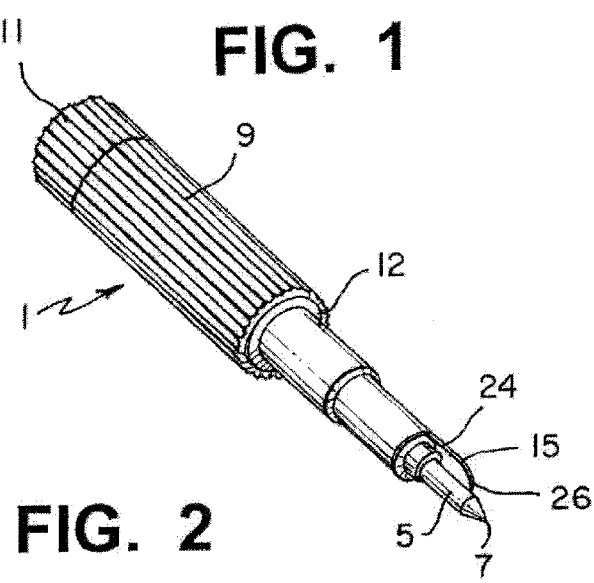
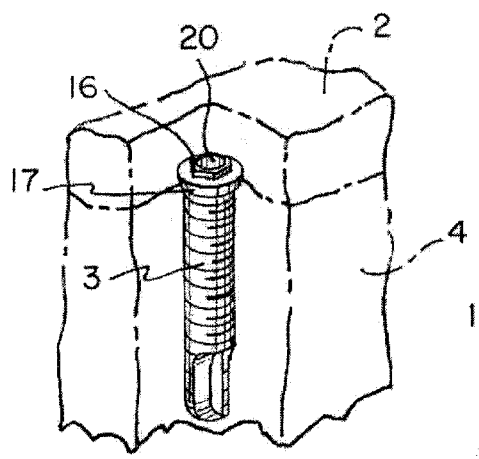
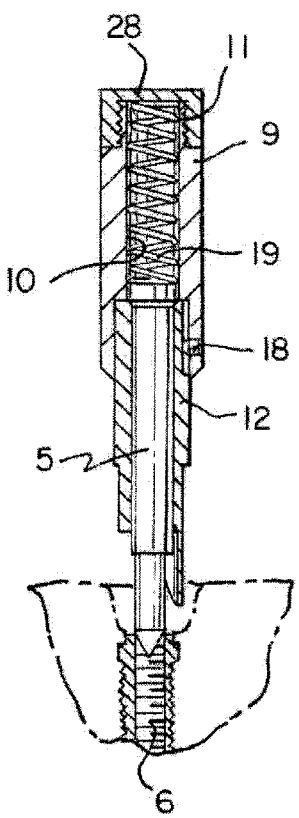
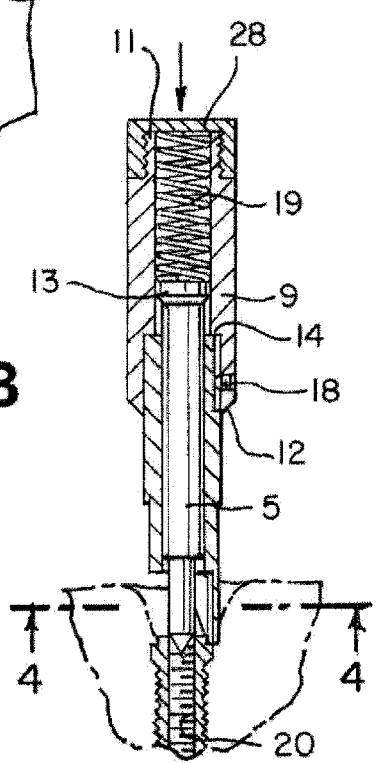

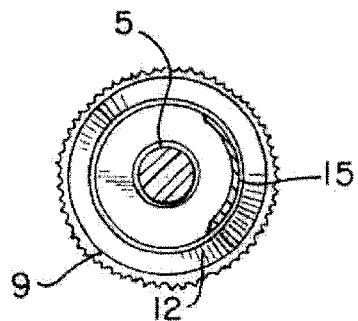
FIG. 4
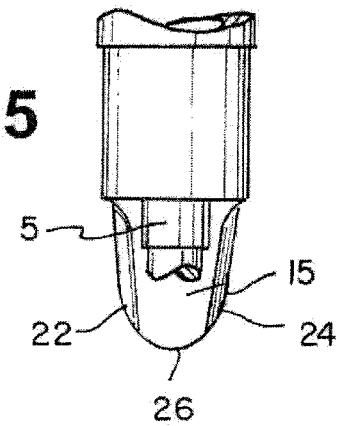
FIG. 5
FIG. 6
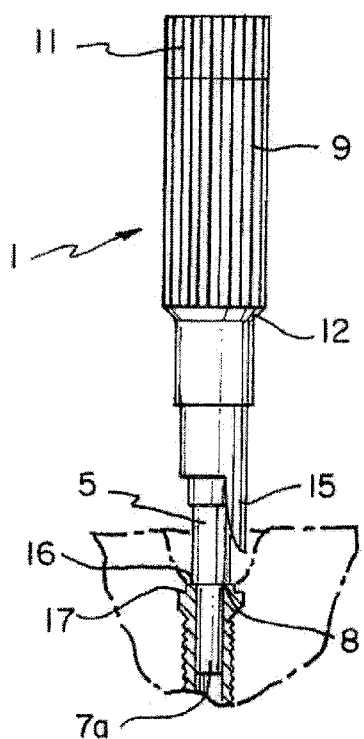

TOOL FOR REMOVING SOFT TISSUE GROWTH AROUND A DENTAL IMPLANT

BACKGROUND OF THE INVENTION

1. Field of the Invention

The present invention relates to dentistry tools, and more specifically to a tool for removing the soft tissue growth around the head of an implant.

2. Discussion of the Related Art

Natural teeth are often lost as a result of dental disease, trauma, or injury. Dental implants are an attractive and functional means to restore a tooth that has been lost. Conventionally, a cavity is drilled in the bone area formally occupied by the lost tooth. Thereafter, an implant is either inserted into the cavity with a friction grip or screwed into the cavity with self-tapping threads.

After an implant is inserted into the bone, a healing period of 4–8 months follows. This time period is necessary for the bone and the implant to join together, securing the implant. During this period of time, a cover screw is placed on top of the implant. The cover screw is connected to the implant by a threaded shaft. The threaded shaft is threadably received within a threaded channel (i.e., an internally threaded blindbore) on the top of the implant so as to prevent the channel from becoming filled with unwanted materials, such as soft tissue, food, et cetera. Soft tissue will, however, naturally grow over the head of the implant and the cover screw. When the bone has sufficiently grown against the implant, the soft tissue that grew over the implant is cut away and the cover screw is removed. A healing abutment is placed on top of the implant and within the threaded channel of the implant. Gum tissue is allowed to heal around the healing abutment for approximately 21 days. The healing abutment, like the cover screw, is a domed retainer having a threaded section for mating with the implant.

Soft tissue once again grows over the sides of the implant during the healing periods just described. Once the gum tissue has healed, a dentist exposes the head of the implant once again to install an abutment on top of the implant. Gum tissue that grew over the healing implant must be removed before installation of the abutment because this soft tissue might prevent a dentist from correctly seating the prosthetic abutment onto the implant.

Currently, a dentist uses a conventional scalpel to remove any soft tissue that has grown around the head of an implant. During use, a scalpel may abrade the implant itself. Additionally, it is rather difficult for the dentist to cut a neat, smooth path about the outer perimeter of the implant.

SUMMARY OF THE INVENTION

Accordingly, a tool is needed that can easily and accurately remove the natural soft tissue growth over the head of the implant, without abrading the implant itself.

According to the present invention, the foregoing advantages are obtained by a dental instrument comprising a blade and an elongated guide connected to the blade. The guide is sized to fit within the bore of a dental implant and is placed at a predetermined radial location with respect to the blade. The guide may selectively translate in a direction parallel to the cutting plane of the blade. The guide includes an outward diameter step or is conically shaped so as to prevent the guide from being inserted further than a predetermined distance into the implant. The guide in accordance with the present invention allows the blade to be selectively placed over a dental implant with more accuracy than other methods available in the art. The blade includes a non-cutting surface that faces the implant during use to prevent the blade from cutting the implant.

Still other advantages of the present invention will become readily apparent to those skilled in this art from the following detailed description, wherein is shown and described only the preferred embodiment of the invention, simply by way of illustration of the best mode contemplated for carrying out the invention. As will be realized, the invention is capable of other and different embodiments, and its several details are capable of modifications in various respects, all without departing from the invention. Accordingly, the drawing and description are to be regarded as illustrative in nature, and not as restrictive.

BRIEF DESCRIPTION OF THE DRAWING FIGURES

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 1 is a perspective view of the preferred embodiment of the invention;

FIG. 2 is a perspective view of an implant set in bone tissue;

FIG. 3A is a front sectional view of the preferred embodiment of the invention being selectively applied to a set implant; and FIG. 3B is an augmented view thereof;

FIG. 4 is a bottom sectional view of the preferred embodiment of the invention taken along line 4—4 of FIG. 3B and looking in the direction of the arrows;

FIG. 5 is a partial front sectional view of the preferred embodiment of the invention; and FIG. 6 is a side elevation view of an alternative embodiment of the invention being selectively applied to a set implant.

DETAILED DESCRIPTION OF THE PRESENTLY PREFERRED EMBODIMENT

Referring now to FIGS. 1–5, a tool 1 is disclosed for cutting soft tissue 2 around an implant 3 that has been inserted into a bone 4. Tool 1 is preferably made of metal or hard plastic. Tool 1 includes a handle 9, a blade 15 fixedly connected to handle 9, and a guide 5 slidably connected to the handle. Guide 5 is sized so that it will properly seat within an internally threaded bore 20 within an implant 6 that has been set within a jawbone so that tool 1 may selectively and accurately remove soft tissue around the dental implant. In one preferred embodiment, a conical tip 7 is formed at the distal end of guide 5, where tip 7 assists in selectively placing guide 5 in a precise location. Alternatively, a planar surface 7a is formed at the reduced diameter distal end of guide 5, as seen in FIG. 6, which will be described below.

Handle 9 is fixedly connected to blade 15 so that the maneuvering of tool 1 can be selectively controlled. The outer surface of handle 9 is preferably knurled to assist the dentist when gripping tool 1. At least the outer material of handle 9 is preferably made of metal, but could also be made of rubber or plastic.

Referring now to FIGS. 3A and 3B, a cylindrical channel 10 within handle 9 is illustrated. Channel 10 is sufficiently long in the axial direction to house the upper end of guide 5. An opening 11 and 12 exists at each axial end of channel 10. Top opening 11 allows for the insertion and removal of guide 5 through channel 10, and, thereafter, a spring 19, to be described below. The top end of guide 5 includes an enlarged diameter conical step 13. Channel 10 includes a reduced diameter step 14 that is smaller in diameter than conical step 13 so that guide 5 is restrained from falling through bottom opening 12 of the channel 10.

As illustrated in FIGS. 1 and 5, blade 15 has a pair of cutting surfaces 22, 24 for severing the soft tissue 2 that has grown over the head of the implant 16. Blade 15 also has a non-cutting surface 26 extending between cutting surfaces 22, 24.

Non-cutting surface 26 is disposed at the distal axial end of blade 15. Cutting surface 22 defines a first cutting plane, and cutting surface 24 defines a second cutting plane. Blade 15 sits above tip of the guide 7 so that tip 7 will reach the head of the implant 16 before blade 15. This action allows a more accurate initial cut of the soft tissue 2 because tool 1 can have tip 7 placed within the bore of the implant 16 to allow the user to align the axis of tool 1 with respect to the axis of implant 16.

Blade 15 is radially spaced from tip 7 so as to be just radially outside of the implant 16 as illustrated in FIG. 3B. Blade 15 has an arcuate shape (see FIG. 4) when viewed in cross-section. Blade 15 is radially positioned on handle 9 so blade 15 sits immediately outside the head of the implant 16, and so that blade 15 sits immediately radially inside an outer step 17 of implant 16. Thus, no excess soft tissue 2 is severed. Moreover, bottom edge 26 of the blade 15 is dull so that the implant head 16 is not affected (e.g., cut or abraded) by radial motion of blade 15 about tip 7.

While the radial position of blade 15 is preferably fixed, it is understood that the radial and/or axial position of blade 15 could be adjustable. Blade 15 is removably attached, for example by a clip or screw 18, to handle 9 and blade 15 is, therefore, preferably disposable. However, blade 15 could be permanently attached to handle 9 and tool 1 could be disposable or reusable with cleaning between uses by conventional techniques, such as autoclaving.

A cap 28 is selectively attached to handle 9 via standard pipe or screw threads. Cap 28 may also be attached to handle 9 via a clip or other fastening devices. A spring 19 is placed within opening 11 at the upper end of channel 10, after guide 5 has been placed within channel 10. Cap 28 is then attached to handle 9 to close opening 11 and maintain spring 19 within handle 9. Spring 19 normally biases guide 5 in a generally downward direction relative to handle 9 toward lower opening 12, as illustrated in FIG. 3A.

Guide 5, in another preferred embodiment of the present invention includes a reduced diameter step 8 at its distal end, as shown in FIG. 6. The reduced diameter distal portion of guide 5 has a diameter smaller than the threaded blind bore diameter of implant 6, which is set in bone 4. One skilled in the art will readily recognize how to size the reduced diameter distal portion of guide 5 to provide a snug fit within the threaded bore of implant 6 so as to permit tool 1, and, thus guide 5 to rotate about its longitudinal axis with respect to implant 6. Similarly, one skilled in the art will know how to size the axial length of the reduced diameter distal end portion of guide 5 to provide a sufficient bearing guide during the rotation of tool 1 about its longitudinal axis. Guide 5, is not threaded, so it does not mesh with nor damage the threads within the bore of implant 6. Guide 5 can only be placed to a predetermined axial distance into the depth of the bore of the implant 6. It is to be understood that the predetermined distance between step 8 and the bottom apex of guide 5 is less than the average depth of a bore of an implant.

Referring now to FIGS. 3A, 3B and 6, in use, tool 1 is selectively placed on top of the head of the implant 16. A dentist will first remove the soft tissue 2 from around the top of the implant 16 and remove a cover screw (not shown) that has been placed on the top of the implant 16 approximately 4–8 months earlier when the implant was first set in the bone 4. Normally it takes about 21 days for exposed gum tissue 2 to heal and bond in the area of the implant 3. A healing abutment (not shown) is threaded into place on the top of the implant 16 for this period. After (approximately) 21 days, the dentist removes the healing abutment, but inevitably there will have been some ingrowth of soft tissue 2. Tool 1, in accordance with the present invention, can be used to remove any of this soft tissue growth.

Guide 5 is placed within the center threaded bore 20 of the implant 6. Tool 1 is further pressed downwardly toward implant 16, as shown in FIG. 3B, thereby compressing spring 19 within channel 10 of handle 9. As spring 19 is compressed, blade 15 moves in a generally downward direction relative to guide 5 and cuts through any contacted soft tissue 2. Tool 1 is moved downward until the non-cutting surface 26 of blade 15 contacts, or is very close to, the top surface of the implant. Handle 9 is then rotated around the head of the implant 16, with guide 5 being the center of rotation. Cutting surfaces 22, 24, thereby sever any soft tissue that has grown over the head of the implant 16. As indicated, the head of implant 16 is unaffected by the motion of blade 15 because in use, the non-cutting surface 26 of blade 15 is the only portion of blade 15 that will contact the implant.

Once the contacted soft tissue 2 is completely severed around the head of the implant 16, handle 9 is moved in a generally upward direction relative to blade 15 and the soft tissue 2. Compressed spring 19 begins to extend, thereby forcing guide 5 to remain in contact with the implant 3 so that blade 15 moves easily and safely away from the location of the severed soft tissue 2. Guide 5 retracts from the bore of the implant 6, upon the full extension of spring 19, whereby tool 1 is removed from the vicinity of the implant 3.

Tool 1 thereby provides an implement that easily and accurately severs soft tissue 2 around the head of an implant 16 in a neat smooth path. The implant top or upper surface is now clean of soft tissue growth 2 and a prosthetic abutment (not shown) can be placed onto the implant 3, and screwed into place.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto. All patents, patent applications, procedures, and publications cited throughout this application are hereby incorporated by reference in their entireties.

What is claimed is:

1. A dental instrument comprising:

a handle having a longitudinal axis;

a blade connected to the handle, the blade having a cutting plane;

an elongated guide slidably connected to the blade, the guide having a distal end being sized to fit within the bore of a dental implant, the guide being essentially coaxial with respect to said handle;

wherein the blade is in a predetermined radial location with respect to the guide and the guide being selectively axially moveable in a direction parallel to a cutting plane of the blade.

2. The dental instrument of claim 1 wherein said guide has a reduced diameter distal end so as to prevent the guide from being inserted further than a predetermined distance into the bore of the implant.

3. The dental instrument of claim 1 wherein the guide has a distal end that is conically-shaped to prevent the guide from being inserted further than a predetermined distance into the bore of the implant.

4. The dental instrument of claim 1 wherein the blade is removably connected to the handle.

5. The dental instrument of claim 1, wherein the blade is in a fixed radial location with respect to the guide.

6. The dental instrument of claim 1, wherein the blade is adjustably positioned in a radial location with respect to the guide.

7. The dental instrument of claim 1, wherein the blade has a first cutting surface defining a first cutting plane, a second cutting surface defining a second cutting plane, a non-cutting surface extending between the first cutting surface and the second cutting surface.

8. The dental instrument of claim 7, wherein the non-cutting surface is at the distal axial end of the blade.

9. The dental instrument of claim 1, wherein the blade is arcuate in shape in axial cross-section.

10. The dental instrument of claim 1, wherein a portion of the guide is slidably disposed within a channel of the handle; and a spring disposed within the channel of the handle for biasing the guide in a distal direction.

11. The dental instrument of claim 10, wherein the guide has a first end and a second end, the first end has an enlarged diameter conical step, the channel has a reduced diameter step that is smaller in diameter than the conical step to limit movement of the guide with the channel.

12. The dental instrument of claim 10, further comprising a cap connected at one end of the handle for maintaining the spring within the channel of the handle.

* * * * *